(12) United States Patent
Gallacher et al.

(10) Patent No.: US 9,504,806 B2
(45) Date of Patent: Nov. 29, 2016

(54) VASCULAR ACCESS SYSTEMS HAVING A GUIDEWIRE ANTI-MIGRATION FEATURE

(71) Applicant: The Queen's Medical Center, Honolulu, HI (US)

(72) Inventors: Thomas Scott Gallacher, Honolulu, HI (US); Jeffrey N. Yu, Honolulu, HI (US)

(73) Assignee: The Queen's Medical Center, Honolulu, HI (US)

( * ) Notice: Subject to any disclaimer, the term of this patent is extended or adjusted under 35 U.S.C. 154(b) by 0 days.

(21) Appl. No.: 14/630,961

(22) Filed: Feb. 25, 2015

(65) Prior Publication Data

US 2015/0165167 A1    Jun. 18, 2015

Related U.S. Application Data

(63) Continuation of application No. 14/044,590, filed on Oct. 2, 2013, now Pat. No. 8,992,480.

(60) Provisional application No. 61/709,073, filed on Oct. 2, 2012.

(51) Int. Cl.
| | |
|---|---|
| *A61M 25/09* | (2006.01) |
| *A61M 39/20* | (2006.01) |
| *A61M 25/00* | (2006.01) |
| *A61M 25/01* | (2006.01) |

(52) U.S. Cl.
CPC ....... *A61M 25/09* (2013.01); *A61M 25/09041* (2013.01); *A61M 39/20* (2013.01); *A61M 25/0097* (2013.01); *A61M 25/0169* (2013.01); *A61M 2025/09125* (2013.01)

(58) Field of Classification Search
CPC ............ A61M 25/09041; A61M 2025/09125; A61M 2025/09116; A61M 25/09
See application file for complete search history.

(56) References Cited

U.S. PATENT DOCUMENTS

| | | | | |
|---|---|---|---|---|
| 2,458,027 A | * | 1/1949 | Quist | A45D 34/04 222/187 |
| 2,667,324 A | | 1/1954 | George | |

(Continued)

FOREIGN PATENT DOCUMENTS

| | | |
|---|---|---|
| EP | 0792657 A2 | 9/1997 |
| EP | 2158932 A2 | 3/2010 |

OTHER PUBLICATIONS

International Search Report for PCT/US2013/063123, mailed Jan. 23, 2014, in 8 pages.

*Primary Examiner* — Kevin C Sirmons
*Assistant Examiner* — William Carpenter
(74) *Attorney, Agent, or Firm* — Knobbe, Martens, Olson & Bear, LLP (57) ABSTRACT

Disclosed herein is a removable cap for connection to an input port of a catheter, comprising a proximal end having a lumen configured to house a guidewire therethrough; a distal end configured to reversibly mate with a luer lock of the input port of a catheter, the distal end having a lumen configured to house the guidewire therethrough; and a tubular body between the proximal end and the distal end, wherein the tubular body comprises an anti-migration feature transformable between a first configuration to allow slidable movement of the guidewire within the cap in a first direction toward the patient, and a second configuration to prevent slidable movement of the guidewire within the cap in the first direction toward the patient. Systems and methods are also disclosed.

13 Claims, 8 Drawing Sheets

(56) References Cited

U.S. PATENT DOCUMENTS

| | | | |
|---|---|---|---|
| 2,987,292 A | 6/1961 | Howard et al. | |
| 3,550,861 A | 12/1970 | Teson | |
| 4,243,034 A | 1/1981 | Brandt | |
| 4,518,145 A | 5/1985 | Keltz et al. | |
| 4,844,092 A | 7/1989 | Rydell et al. | |
| 4,858,810 A * | 8/1989 | Intlekofer | A61B 17/22 226/127 |
| 5,159,861 A * | 11/1992 | Anderson | A61B 17/22 226/127 |
| 5,205,831 A | 4/1993 | Ryan et al. | |
| 5,338,314 A * | 8/1994 | Ryan | A61M 39/0613 604/167.06 |
| 5,346,498 A | 9/1994 | Greelis et al. | |
| 5,389,100 A | 2/1995 | Bacich et al. | |
| 5,397,310 A | 3/1995 | Chu et al. | |
| 5,489,274 A * | 2/1996 | Chu | A61M 39/0613 604/167.05 |
| 5,499,632 A | 3/1996 | Hill, III | |
| 5,634,475 A * | 6/1997 | Wolvek | A61M 25/09041 600/585 |
| 5,827,234 A | 10/1998 | Loos et al. | |
| 6,746,466 B2 | 6/2004 | Eidenschink et al. | |
| 7,172,577 B2 | 2/2007 | Mangano et al. | |
| 7,678,100 B2 | 3/2010 | Chin et al. | |
| 7,959,667 B2 | 6/2011 | Ta et al. | |
| 8,206,283 B2 | 6/2012 | Windheuser et al. | |
| 8,343,041 B2 * | 1/2013 | Byers | A61B 1/00128 600/154 |
| 2002/0177869 A1 | 11/2002 | Eidenschink et al. | |
| 2004/0006329 A1 | 1/2004 | Scheu | |
| 2006/0224176 A1 | 10/2006 | Fung et al. | |
| 2007/0161969 A1 | 7/2007 | Andersen | |
| 2008/0262430 A1 * | 10/2008 | Anderson | A61B 17/3415 604/164.1 |
| 2010/0121279 A1 | 5/2010 | Chin et al. | |
| 2011/0040238 A1 | 2/2011 | Wulfman et al. | |
| 2011/0208286 A1 | 8/2011 | Ta et al. | |
| 2012/0071857 A1 * | 3/2012 | Goldfarb | A61B 17/24 604/514 |
| 2012/0078232 A1 | 3/2012 | Schulting | |

* cited by examiner

VASCULAR ACCESS SYSTEMS HAVING A GUIDEWIRE ANTI-MIGRATION FEATURE

PRIORITY CLAIM

This application claims the benefit under 35 U.S.C. §120 as a continuation application of U.S. application Ser. No. 14/044,590 filed on Oct. 2, 2013 and issued as U.S. Pat. No. 8,992,480 on Mar. 31, 2015, which in turn claims priority under 35 U.S.C. §119(e) as a nonprovisional application of U.S. Prov. Pat. App. No. 61/709,073 filed on Oct. 2, 2012. All of the priority applications are hereby incorporated by reference in their entireties.

BACKGROUND

Field of the Invention

This invention relates generally to a catheter and a feature to prevent undesired guidewire migration.

SUMMARY OF THE INVENTION

Disclosed herein is a removable cap for connection to an input port of a catheter, comprising a proximal end having a lumen configured to house a guidewire therethrough; a distal end configured to reversibly mate with a luer lock of the input port of a catheter, the distal end having a lumen configured to house the guidewire therethrough; and a tubular body between the proximal end and the distal end, wherein the tubular body comprises an anti-migration feature transformable between a first configuration to allow slidable movement of the guidewire within the cap in a first direction toward the patient, and a second configuration to prevent slidable movement of the guidewire within the cap in the first direction toward the patient. In some embodiments, the second configuration of the anti-migration feature allows slidable movement of the guidewire within the cap in a second direction opposite the first direction. In some embodiments, the anti-migration feature comprises a spring-loaded element. In some embodiments, the cap further comprises a plurality of arms configured to transmit a radial inward force to the guidewire when a force is applied on the arms by the spring-loaded element. In some embodiments, the tubular body comprises a movable wall transformable from a first radially compressed configuration for preventing axial movement of the guidewire and a second radially enlarged configuration for allowing axial movement of the guidewire. In some embodiments, the anti-migration feature comprises a threaded wingnut. In some embodiments, the anti-migration feature comprises a zone of the lumen having a tapered sidewall and a plurality of beads operably connected to the sidewall, the beads selectively exerting a radially compressive force on the guidewire when the guidewire moves in the first direction. Also disclosed herein is a catheter system comprising a catheter, a guidewire, and a removable cap.

DETAILED DESCRIPTION

Catheters, including central venous catheters, are used extensively for, among other things, dialysis access, intravenous fluids, vasopressors, chemotherapy, parenteral nutrition, and long term antibiotics.

Guidewires are typically used to facilitate insertion of a medical device, such as a catheter, into a body lumen, such as a blood vessel for example. The classic or modified Seldinger technique is a common way to deploy the medical device over the guidewire. In some embodiments, catheter insertion using the Seldinger technique can include one or more of the following steps:

Administer local anesthestic
Locate vein using finder needle connected to a syringe
Remove syringe once needle appropriately situated in body lumen
Confirm placement of needle (e.g., using hemodynamic monitoring such as central venous pressure, color, or absence of pulsatile blood flow for example)
Advance guidewire through needle lumen into the target vessel
Hold guidewire in place, remove needle
Enlarge cutaneous puncture site (e.g., via a scalpel)
Insert dilator over the guidewire to further enlarge site
Remove dilator
Thread tip of catheter over the guidewire; grasp catheter near skin and advance into vein with a slight twisting motion
Remove guidewire
Place caps on input ports to reduce risk of air embolism
Aspirate catheter ports to remove air
Flush ports, e.g., with saline or heparin A potential life-threatening complication with the use of central venous catheters is migration of the guidewire (or breakage or fracture of the guidewire or catheter) with the intravascular fragment migrating centrally as a foreign body embolus, such as when the operator may not be fully attentive to the guidewire. It has been estimated that this complication occurs with a frequency of approximately $1/1000$-$2/1000$. Most often the intravascular fragment (or end of the guidewire) becomes lodged within the right heart where it may produce an arrhythmia or compromise a valve. Less frequently, the intravascular fragment (or end of the guidewire) lodges more distally within a pulmonary artery with the risk of causing a pulmonary infarction.

There is a risk of undesired guidewire migration at any step where the guidewire is at least partially in the body, after the guidewire is advanced through the needle lumen into the target vessel. It is often inconvenient to necessitate a second operator to be present and "sterile" for the sole purpose of holding onto the proximal end of the guidewire for preventing unwanted guidewire migration during a catheter insertion or exchange procedure. Furthermore, other methods of preventing unwanted guidewire migration, such as clamping the proximal end of the guidewire with a hemostat to lock the guidewire in place can undesirably damage the guidewire.

Disclosed herein are systems and methods for preventing undesired migration of a guidewire utilized during insertion or exchange of a catheter utilized to cannulate a body lumen. In some embodiments the systems can be in the form of a retention element that could be fitted to one end of a catheter. For example, the retention element could be an integral or removable cap configured to mate with the luer lock of one of the catheter's input ports (e.g., screwed into the hub of the catheter). In some embodiments, the retention element could be pre-attached to the catheter to be threaded over the guidewire. The inventive caps could replace conventional catheter caps and be compatible with a variety of existing catheters, such as central venous lines, dialysis catheters, heart catheterization catheters, or arterial lines, to name some non-limiting examples.

The retention element can be configured to reversibly prevent guidewire movement in a single direction (e.g., distal guidewire movement into the vessel), or in multiple directions (e.g., movement both into the vessel and outside of the vessel). In some embodiments, the retention element can allow free movement of the guidewire in a first direction out of the patient when the catheter is threaded over the wire, but reversibly prevents movement of the guidewire in a second opposite direction (e.g., into the patient). In some embodiments, the retention element may allow free movement of the guidewire into the patient if a release mechanism on the retention device is activated.

While guidewires are more commonly used to cannulate a vein or an artery, other body lumens including a lymphatic vessel, biliary tree, etc. can also be cannulated and embodiments described herein can be used to prevent guidewire migration in systems and methods thereof, and for that matter, any procedure in which a guidewire is used to deliver a medical or non-medical device.

Figure 1:
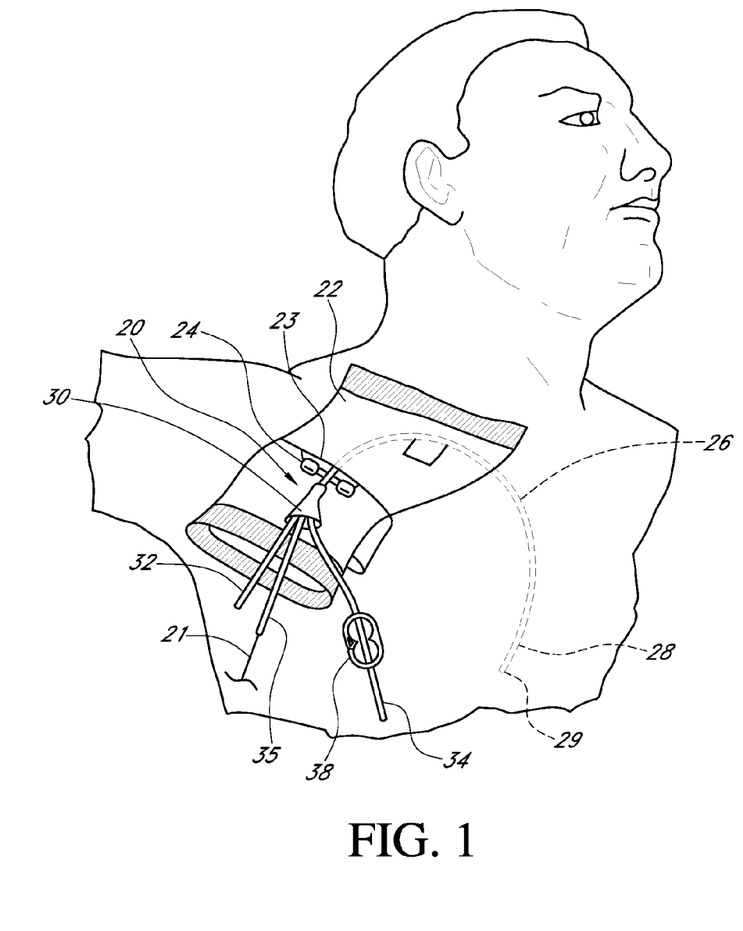
FIG. 1 illustrates a catheter secured to a dressing by an attachment fitting having wing tabs.
Figure 2:
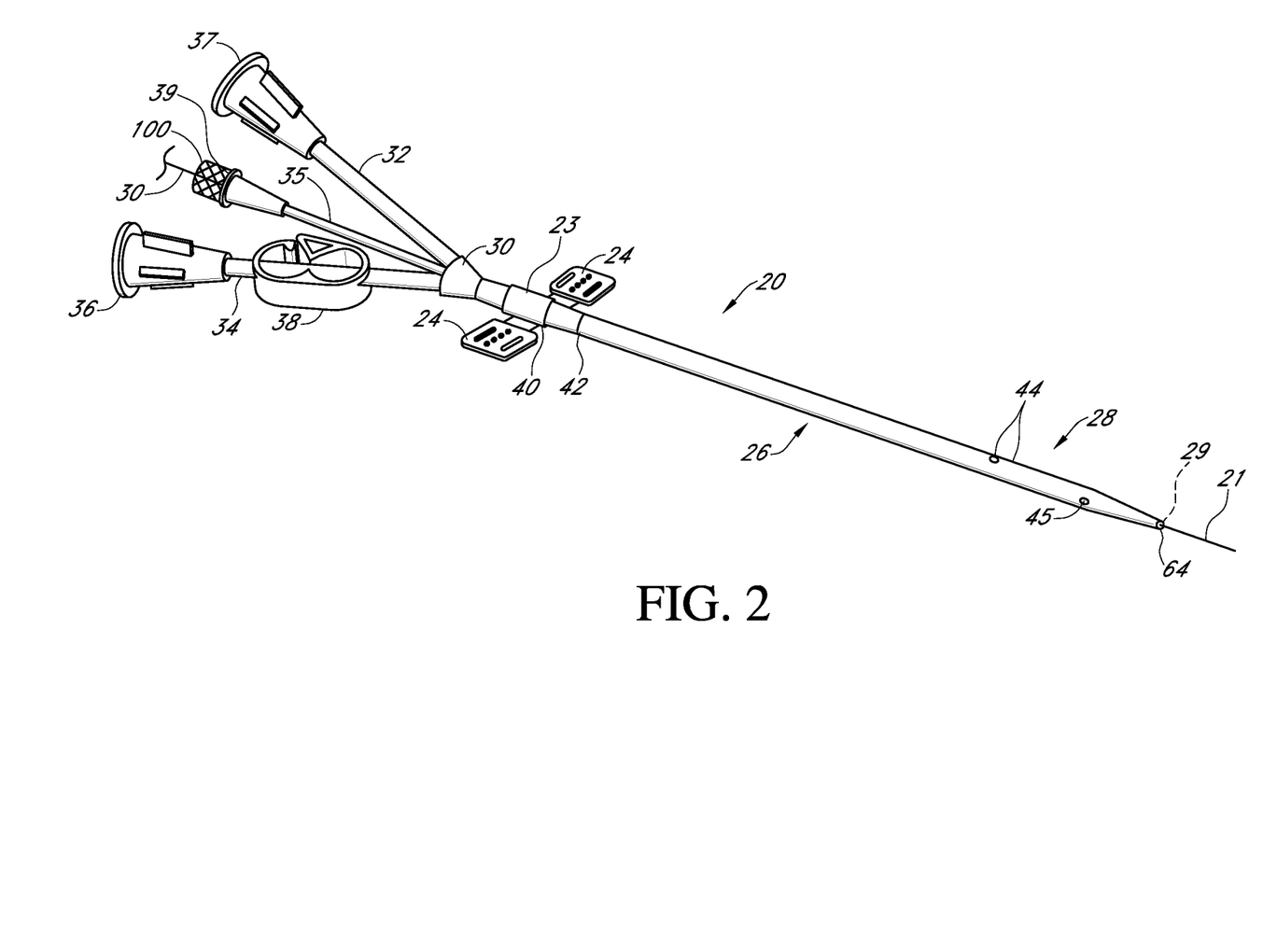
FIG. 2 shows an embodiment of a catheter 20 in greater detail.

One common type of catheter inserted over a guidewire is a central venous catheter, which is typically inserted via an internal jugular, subclavian, axillary, or femoral vein approach. One embodiment of a "triple lumen" dialysis catheter is illustrated in FIGS. 1-2. A central venous catheter, such as those described, for example, in U.S. Pat. No. 6,206,849 to Martin et al., hereby incorporated by reference in its entirety, can include one or more input ports operably connected to a conduit fluidly connected to the catheter body. FIG. 1 of the drawings illustrates a triple lumen catheter, indicated generally by reference numeral 20, according to some embodiments, and showing by way of example, a patient receiving the catheter in the sub clavian vein using a guidewire 21. The catheter is to be used for hemodialysis treatment and could also be entered in a similar fashion in the femoral vein or internal jugular vein, for example. Some non-limiting examples of dialysis catheters that can be used or modified for use herein include Mahurkar™ or Quinton™ catheters, or tunneled catheters such as Hickman™ or Groshong™ catheters for example. In some embodiments, the catheter could be utilized for right or left heart catheterization, such as a Swan-Ganz™ catheter for example. In some embodiments, the catheter could be a central venous catheter (either centrally or peripherally inserted) such as the ARROW® line of catheters manufactured by Teleflex Inc. (Limerick, Pa.).

In some embodiments, as illustrated in FIG. 1 the catheter 20 is secured to a conventional dressing 22 by an attachment fitting 23 having wing tabs 24, and the dressing 22, in turn, is secured to the skin of the patient. As shown, the catheter 20 passes through the dressing 22 and, as can be seen in broken outline, an elongate and flexible cylindrical body 26, formed of a polyurethane extrusion for example, is inserted through the skin and into the subclavian vein in the downstream direction. The catheter 20 has at its distal end 28 a conical tapered tip 29 which is described in greater detail below. The other end of the body 26 is a generally trident-shaped branching connector 30, which protrudes outwardly from and is secured by dressing 22. Cylindrical blood extraction and return tubes 32, 34 and an intravenous (IV) tube 35 are attached to the trident-shaped branching connector 30. These tubes are connected to lumens running through the body 26.

FIG. 2 shows an embodiment of a catheter 20 in greater detail. The body 26 has at its proximal end the connector 30 for receiving the blood extraction and return tubes 32, 34. These tubes terminate at their outer ends in respective female luer fittings 36, 37 for connection to complementary male luer fittings (not shown) leading to a dialysis machine, and carry closure clamps 38 (one of which is shown) to selectively close the tubes.

The IV tube 35 terminated at its outer end in a luer lock fitting 39 for receiving a syringe or male luer lock connector.

The wing tabs 24, sometimes known as suture wings, can be formed integrally with a central tubular portion 40 which can rotate on the body 26 and is retained in place by a shoulder on the end of the connector 30 and a second shoulder in a reinforcing portion 42 so that the catheter 20 can be rotated relative to the tabs 24. This rotation is sometimes necessary after insertion of the catheter 20 to re-orientate intake side apertures in the distal end 28 if the apertures happen to be occluded by engagement with the wall of the vein.

The reinforcing portion 42 can be blended into the body 26 over the length of the portion and assists in strengthening the catheter to minimize the likelihood of kinking. Also, the portion 42 assists in sealing the puncture site where the catheter enters the patient.

The tube 35 can be aligned with a central lumen to permit the guidewire 21 to pass through the catheter. The guidewire 21 exits the distal end 28 of catheter body 26 through a tip aperture 64 at the apex of tip 29 which can be essentially conical in some embodiments so that the catheter can slide over the wire and into the patient during insertion. The extraction and return tubes 32, 34 are linked at connector 30 with lumens in the body 26 to connect with respective groups of side apertures 44, 45 (some of which can be seen in this view) near the distal end of the catheter 28. As a result, when inserted and in use, blood can be removed and returned in a closed loop with a haemodialysis machine using the tubes 32, 34. Between treatments the tube 35 is available for intravenous infusion of liquid medicaments. While a catheter having 3 lumens is shown, one will appreciate that catheters having a different number of access ports, such as 1, 2, 3, 4, or more access ports are also possible.

In some embodiments, the catheter could have one or more features to prevent guidewire migration into the body lumen, such as a cap 100 (shown schematically in FIG. 2) with a lumen therethrough configured to allow movement of the guidewire 21 in a first direction (e.g., proximally, or out of the body lumen, and toward the operator) but also configured to inhibit or prevent movement of the guidewire 21 in a second direction (e.g., distally, or toward the body lumen) which can be an opposite direction from the first direction. In some embodiments, the cap 100 provides a force sufficient to inhibit or prevent guidewire 21 movement without deforming/causing damage to the guidewire 21. The cap 100 could either be removable or non-removable (e.g., integrally formed with the catheter) in some embodiments, and if removable configured to mate with luer lock fitting 39 of tube 35.

Figure 3:
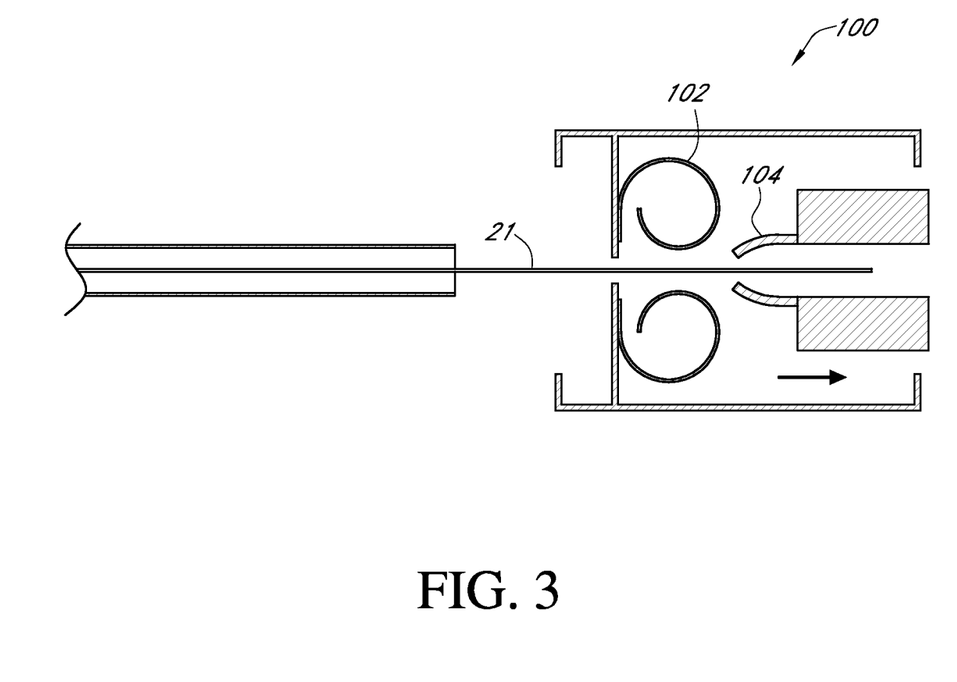
FIG. 3 illustrates an embodiment of a guidewire anti-migration cap that can include a spring or other biasing element configured to exert a force on a compression element.

In one embodiment, as illustrated in FIG. 3, a guidewire anti-migration cap 100 can include a spring 102 or other biasing element configured to exert a force on compression element, e.g., arms 104 having a channel for the guidewire to pass therethrough. The spring 102—arms 104 system can be configured such that it inhibits any guidewire movement (e.g., locks the guidewire in place), or in some embodiments selectively allows for guidewire 21 movement proximally, or out of the patient, while inhibiting guidewire 21 movement distally, or into the patient. In some embodiments, the cap 100 can function similarly to that of a one-way valve.

Figure 4A:
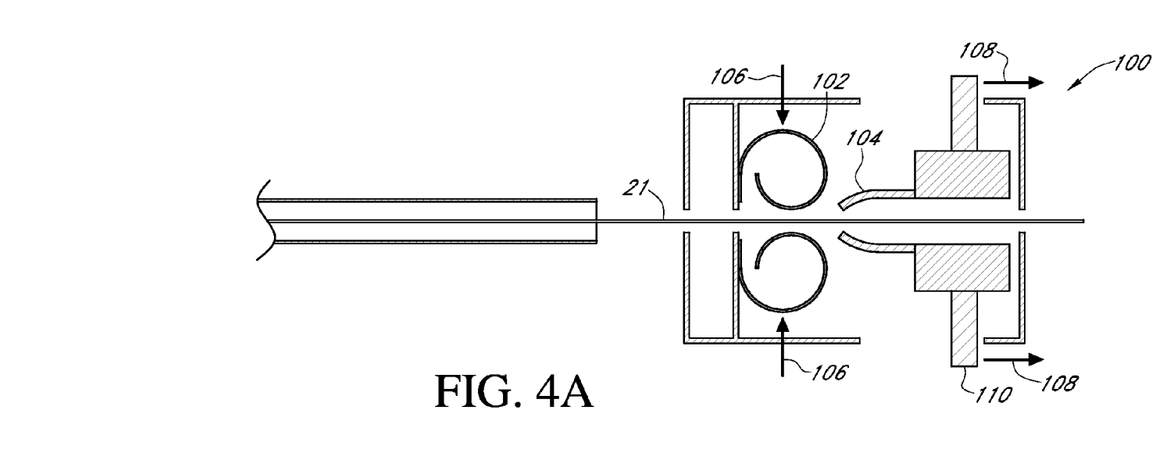
FIGS. 4A-4B illustrate an embodiment of a guidewire anti-migration cap.
Figure 4B:
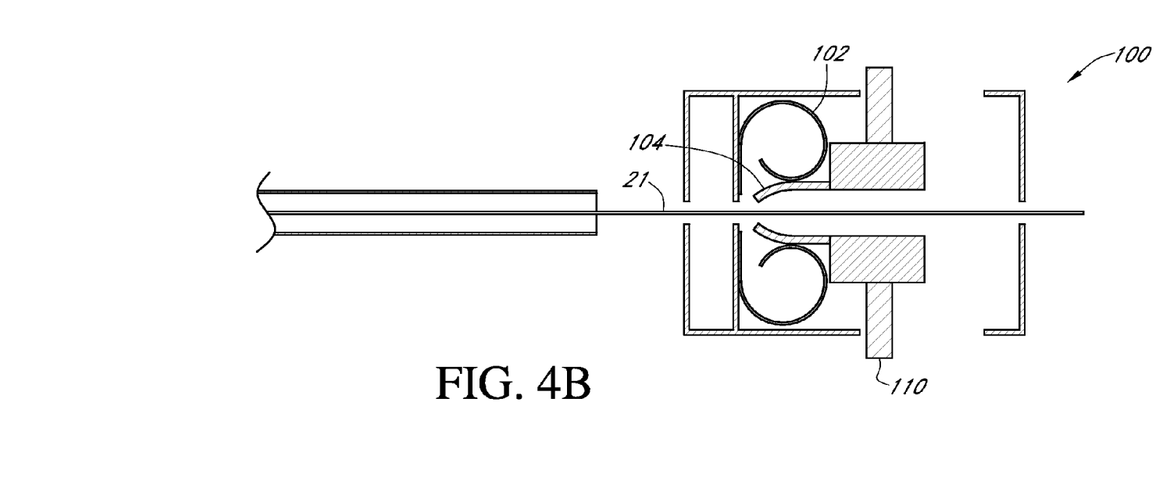

FIGS. 4A-4B illustrate a guidewire anti-migration cap similar to that of FIG. 3. As illustrated in FIG. 4A, cap 100 can include a spring 102 that can be biased to exert a force in the direction of arrows 106. Structure 104 can have elements, such as arms configured to exert a force, such as a radial inward force when compressed by spring 102 to inhibit movement of the guidewire 21. In some embodiments, structure 104 has a first position, movable in the direction of arrows 108 to allow for the guidewire 21 to also slide proximally in the direction of arrows 108, such as when a user exerts a force on control 110. As illustrated in FIG. 4B, structure is in a second position, where spring 102 actually exerts a force on structure 104 in order to inhibit either proximal or bi-directional movement of guidewire 21. In some embodiments, the cap 100 can have a default biased position as shown in FIG. 4B where guidewire 21 movement (either proximally or in both directions) is inhibited if no force is exerted by a user on control 110.

Figure 5:
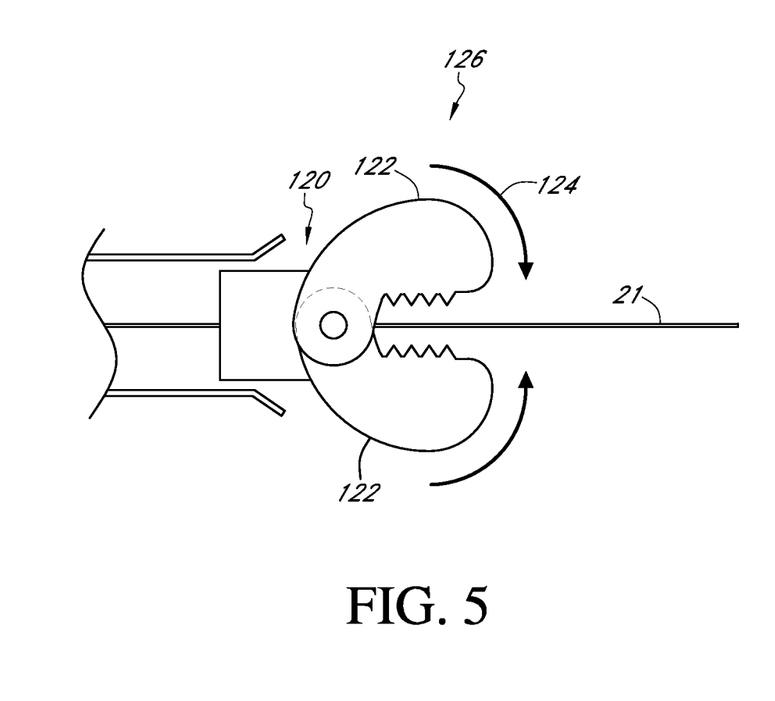
FIG. 5 illustrates another embodiment of a cap that includes a compressive element having a plurality of jaws.

FIG. 5 illustrates another embodiment of a cap 126 that includes a compressive element 120 having a plurality of jaws 122. In some embodiments, jaws 122 can be naturally biased in the direction of arrows 124 and configured to inhibit either proximal or bi-directional movement of guidewire 21. Jaws 122 can be movable between a first open position and a second closed position.

Figure 6A:
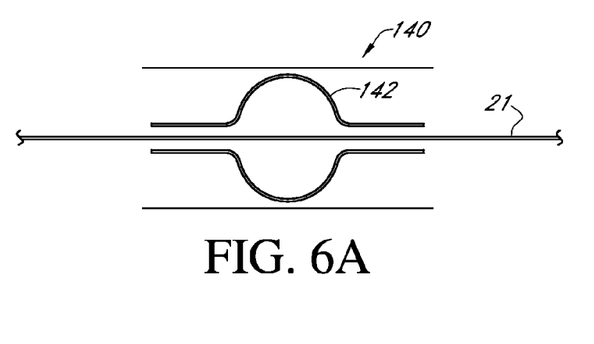
FIGS. 6A-6D illustrate an embodiment of a cap having one, two, or more movable walls configured to reversibly move between a first, open position as shown in FIG. 6A (as well as the cross-sectional view of FIG. 6C) and a second, closed position as shown in FIG. 6B (as well as the cross-sectional view of FIG. 6D).
Figure 6B:
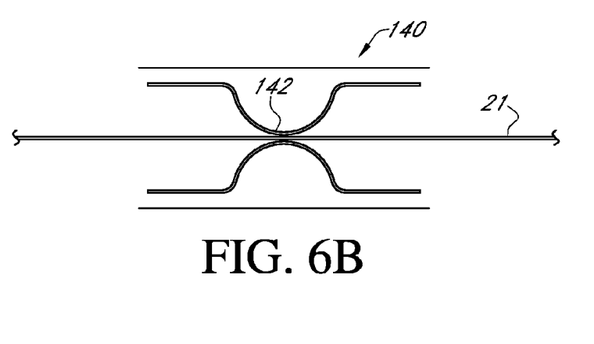
Figure 6C:
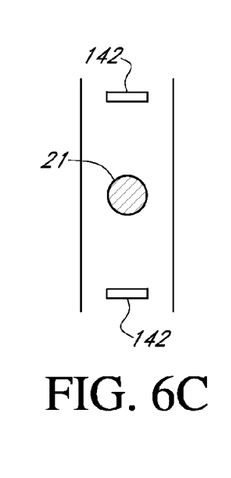
Figure 6D:
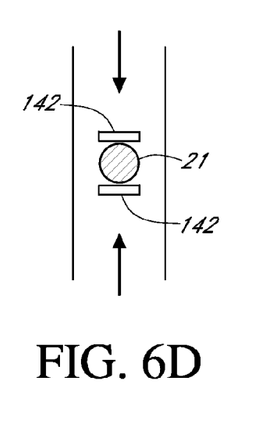

FIGS. 6A-6D illustrate an embodiment of a cap 140 having one, two, or more movable walls 142 configured to reversibly move between a first, open position as shown in FIG. 6A (as well as the cross-sectional view of FIG. 6C) and a second, closed position as shown in FIG. 6B (as well as the cross-sectional view of FIG. 6D) and configured to inhibit either proximal or bi-directional movement of guidewire 21 when in the closed position. In some embodiments, the walls are spring-loaded or have another mechanism such that manual pressure by an operator on the radial outward surface of the walls 142 is sufficient to move the walls 142 between the aforementioned positions.

Figure 7:
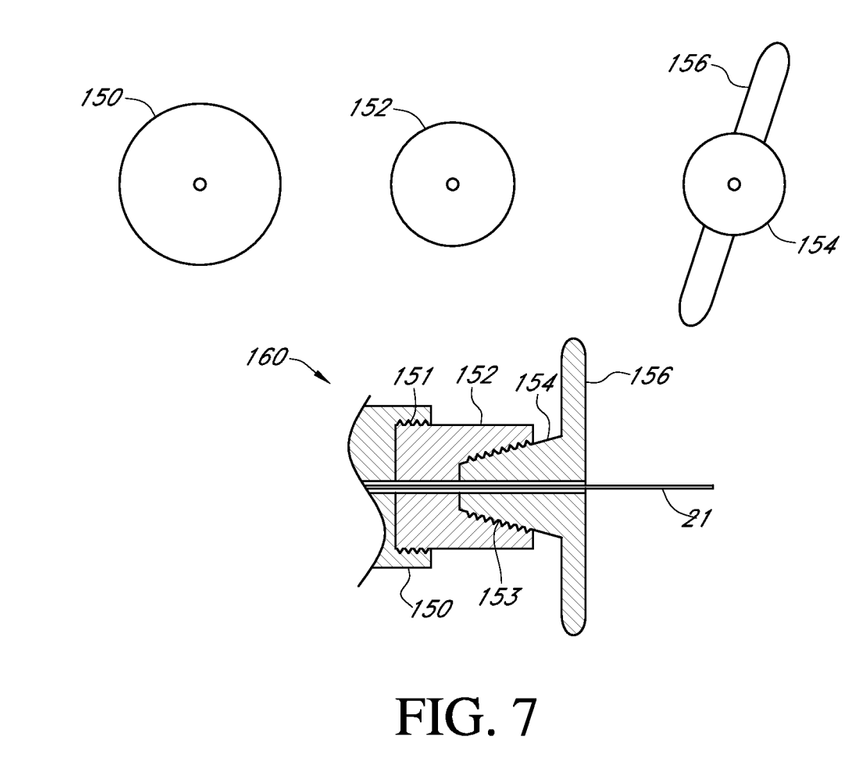
FIG. 7 illustrates an embodiment of a cap or input port of a catheter that includes a first threaded segment, a second threaded segment, and a third threaded segment.

FIG. 7 illustrates an embodiment of a cap 160 or input port of a catheter that includes a first threaded segment 150, a second threaded segment 152, and a third threaded segment 154. The first threaded segment 150 can have threads 151 oriented in a first direction. The second threaded segment 152 is configured to mate with the threads 151 of the first threaded segment 150; the third threaded segment 154 can have threads configured to mate with the threads 153 of the second threaded segment. In some embodiments, the third treaded segment 154 can be a wingnut, thumbscrew, or similar structure and have one, two, or more wings 156 such that it can be easily tightened or loosened without requiring tools. In some embodiments, the second threaded segment 152 has threads in a first direction (e.g., clockwise), while the third threaded segment 154 has threads in a second direction opposite the first direction (e.g., counterclockwise). As such, rotating (e.g., screwing) the second threaded segment 152 and the third threaded segment 154 with respect to the first threaded segment 150 will tighten the second threaded segment 152 while keeping the third threaded segment 154 loose and allowing guidewire 21 to be inserted into the body lumen and move axially with respect to the cap 160. Rotating (e.g., screwing) the second threaded segment 152 in the second direction opposite the first direction (e.g., counterclockwise) can tighten the third threaded segment 154 against the guidewire 21, removing the entire cap 160 and cinching the third threaded segment 154 onto the guidewire 21, such that the guidewire 21 can move proximally out of the body lumen, but not distally into the body lumen.

Figure 8:
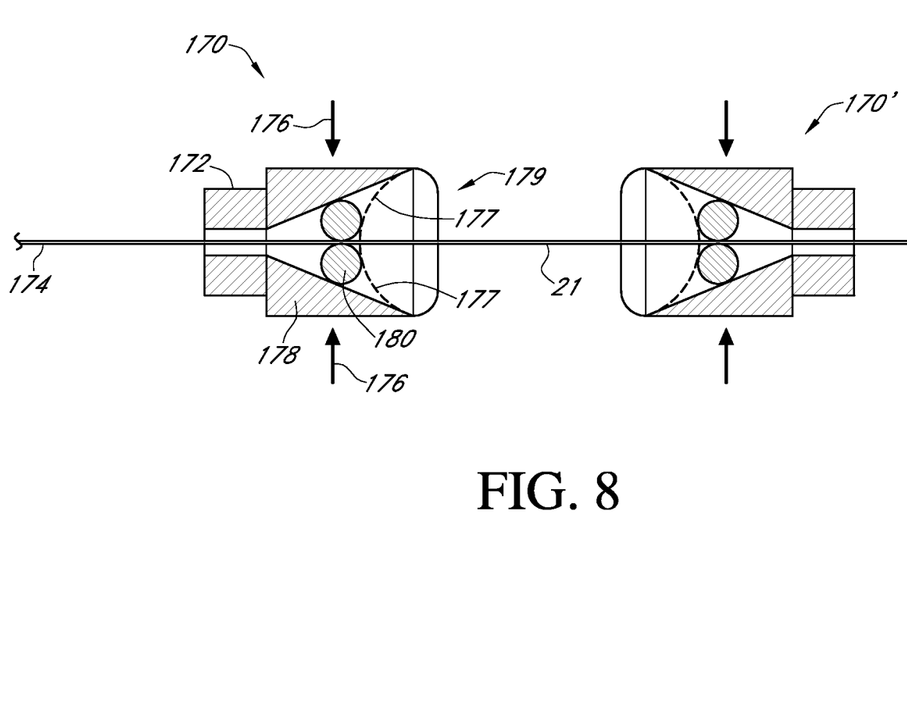
FIG. 8 illustrates another embodiment of a guidewire retention element for a catheter system.

FIG. 8 illustrates another embodiment of a guidewire retention element 170 for a catheter system. The retention element 170 could include a cap and can have a distal end 172 that can be threaded in some embodiments, e.g., to mate with a luer lock of an input port of a catheter (not shown) and a lumen 179 configured to allow passage of a guidewire 21 therethrough. The cap could include a tapered zone with a sidewall 178 that is cone-shaped in some embodiments, with a diameter that increases from the proximal end 172 (toward the patient 174) distally. Within the lumen 179 are a plurality of beads 180 that can be fixed or operably connected to the sidewall 178 such that the beads 180 are configured to selectively exert a radially inward compressive force on the guidewire 21 as they press against the narrower diameter portion of the sidewall 178 when the guidewire 21 moves toward distally, e.g., toward the patient 174. In some embodiments, the retention element 170 can also include one or more springs 177, dome, or other elements that exerts tension on the beads 180 when the guidewire 21 is stationary, such that the guidewire 21 is held or locked in place, preventing any slippage of the guidewire 21 into the patient, such as when the patient moves, breathes, etc. However, the beads 180 can be configured to freely allow movement of the guidewire 21 in a proximal direction, e.g., away from the patient end 174. In some embodiments, squeezing or otherwise exertion a force in the direction of arrows 176 causes release of the guidewire 21. In some embodiments, a system could include two or more retention elements 170 as illustrated with the widest diameter portions of the tapered zones 178 facing each other, wherein the first retention element 170 selectively inhibits guidewire movement in a first direction and the second retention element 170' selectively inhibits guidewire movement in a second direction. The retention elements 170, 170' could be discrete as illustrated, or integrally formed into a single retention element in some embodiments.

While some of the embodiments herein have been described generally as within a cap, the anti-migration feature need not necessarily be positioned on a luer lock fitting of one of the input ports. In some embodiments, the feature could be present on another location on the catheter 20, such as within tubes 32, 34, or 35, at connector 30, or on the catheter body 26 of FIG. 1 for example. In some embodiments, the cap or other anti-migration feature can include an anti-infective such as an antibiotic to reduce the risk of catheter-associated infection.

Although certain embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or subcombinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above. For all of the embodiments described above, the steps of any methods need not be performed sequentially.

What is claimed is:

1. A removable cap for connection to an input port of a catheter, comprising:
   a proximal end having a lumen configured to house a guidewire therethrough;
   a distal end configured to reversibly mate with a luer lock of the input port of the catheter, the distal end having a lumen configured to house the guidewire therethrough; and
   a tubular body between the proximal end and the distal end,
   wherein the tubular body comprises an anti-migration feature comprising a spring-loaded element and a plurality of arms configured to transmit a radial inward force to the guidewire when a force is applied on the arms by the spring-loaded element, the anti-migration feature transformable between a first configuration to allow slidable movement of the guidewire within the cap in a first direction toward the patient, and a second configuration to prevent slidable movement of the guidewire within the cap in the first direction toward the patient,
   wherein the plurality of arms are circumscribed by the tubular body.

2. The removable cap of claim 1, wherein the second configuration of the anti-migration feature allows slidable movement of the guidewire within the cap in a second direction opposite the first direction.

3. The removable cap of claim 1, wherein the tubular body comprises a movable wall transformable from a first radially compressed configuration for preventing axial movement of the guidewire to a second radially enlarged configuration for allowing axial movement of the guidewire.

4. A catheter system comprising: a catheter, a guidewire, and the removable cap of claim 1.

5. The removable cap of claim 1, wherein the anti-migration feature is configured to be transformable between the first configuration and the second configuration when a user exerts a force on a movable control operably connected to the cap.

6. The removable cap of claim 1, wherein the plurality of arms is operably connected to a control, wherein exertion of a force on the control moves the plurality of arms from a first position engaged with the spring-loaded element to a second position disengaged from the spring-loaded element.

7. The removable cap of claim 6, wherein the control extends radially outwardly from the tubular body.

8. A removable cap for connection to an input port of a catheter, comprising:
   a proximal end having a lumen configured to house a guidewire therethrough;
   a distal end configured to reversibly mate with a luer lock of the input port of the catheter, the distal end having a lumen configured to house the guidewire therethrough; and
   a tubular body between the proximal end and the distal end,
   wherein the tubular body comprises an anti-migration feature comprising a spring-loaded element and a plurality of arms configured to transmit a radial inward force to the guidewire when a force is applied on the arms by the spring-loaded element, the anti-migration feature transformable between a first configuration to allow slidable movement of the guidewire within the cap in a first direction toward the patient, and a second configuration to prevent slidable movement of the guidewire within the cap in the first direction toward the patient,
   wherein the tubular body comprises a movable wall transformable from a first radially compressed configuration for preventing axial movement of the guidewire to a second radially enlarged configuration for allowing axial movement of the guidewire.

9. The removable cap of claim 8, wherein the second configuration of the anti-migration feature allows slidable movement of the guidewire within the cap in a second direction opposite the first direction.

10. A catheter system comprising: a catheter, a guidewire, and the removable cap of claim 8.

11. The removable cap of claim 8, wherein the anti-migration feature is configured to be transformable between the first configuration and the second configuration when a user exerts a force on a movable control operably connected to the cap.

12. The removable cap of claim 8, wherein the plurality of arms is operably connected to a control, wherein exertion of a force on the control moves the plurality of arms from a first position engaged with the spring-loaded element to a second position disengaged from the spring-loaded element.

13. The removable cap of claim 12, wherein the control extends radially outwardly from the tubular body.

* * * * *